(12) United States Patent
Albrecht et al.

(10) Patent No.: US 7,029,877 B2
(45) Date of Patent: Apr. 18, 2006

(54) METHODS AND REAGENTS FOR PROTEASE INHIBITION

(75) Inventors: Hugo Albrecht, Riehen (CH); Ulrich Hengst, Basel (CH); Denis Monard, Fullinsdorf (CH)

(73) Assignee: Novartis Forschungsstiftung Zweigniederlassung Friedrich Miescher Instittue for Biomedical Research, Basel (CH)

( * ) Notice: Subject to any disclaimer, the term of this patent is extended or adjusted under 35 U.S.C. 154(b) by 426 days.

(21) Appl. No.: 10/362,642

(22) PCT Filed: Aug. 30, 2001

(86) PCT No.: PCT/EP01/10043

§ 371 (c)(1),
(2), (4) Date: Feb. 24, 2003

(87) PCT Pub. No.: WO02/18623

PCT Pub. Date: Mar. 7, 2002

(65) Prior Publication Data

US 2005/0037009 A1    Feb. 17, 2005

(51) Int. Cl.
  C12N 15/09  (2006.01)
  G01N 33/53  (2006.01)
  C07K 14/00  (2006.01)
(52) U.S. Cl. ............... 435/69.2; 435/7.1; 530/350
(58) Field of Classification Search ............... 435/69.2, 435/7.1; 530/350
See application file for complete search history.

(56) References Cited

FOREIGN PATENT DOCUMENTS

| EP | 0 628 631 | 12/1994 |
|----|-----------|---------|
| EP | 0 965 597 | 12/1999 |
| JP | 5 092 993 | 4/1993  |
| WO | WO 96 29347 | 9/1996 |

OTHER PUBLICATIONS

Matsukkawa et al., "Increased Expression of Hippocampal Cholinergic Neurostimulating Peptide-Related Components and their Messenger RNAS in the Hippocampus of Aged Senescence-Accelerated Mice", Neuroscience, vol. 88, No. 1, pp. 79-92, (1999).

Section Ch, Week 199320, Derwent Publications Ltd., London, GB; Class BO4, An 1993-162126 XP002201326 & JP 05 092993 A (Tosoh Corp, 1993—Abstract).

EBI; Sequence ID PEBP_MOUSE, (1997), Lin and Frischauf, Database accession No. P70296 XP002201325—Abstract.

Bruun et al.,, "A high-Affinity Inhibitor of Yeast Carboxypeptidase Y is Encoded by TFS1 and Shows Homology to a Family of Lipid Binding Proteins", Biochemistry, vol. 37, No. 10, pp. 3351-3357, (1998).

Banfield et al., "Function from Structure? The Crystal Structure of Human Phosphatidylethanolamine-binding protein Suggests a Role in Membrane Signal Transduction", Structure, vol. 6, No. 10, pp. 1245-1254, (1998).

Hengst Ulrich et al., "The Phosphatidylethanolamine-Binding Protein is a Prototype of a Novel Family of Serine Protease Inhibitors", Journal of Biological Chemistry, vol. 276, No. 1, pp. 535-540, (2001).

Turgeon et al., "The Role of Thrombin-Like (serine) Proteases in the Development, Plasticity and Pathology of the Nervous System", Brain Research Reviews, vol. 25, pp. 85-95, (1997).

Wagner et al., "Protease Nexin-1, an Antithrombin with Neurite Outgrowth Activity, is Reduced in Alzheimer Disease", Proc. Natl. Acad. Sci. USA, vol. 86, pp. 8284-8288, (1989).

Davies et al., "Serine Proteases in Rodent Hippocampus", The Journal of Biological Chemistry, vol. 273, No. 36, pp. 23044-23011, (1998).

Gloor et al., "A Gilla Derived Neurite Promoting Factor with Protease Inhibitory Activity Belongs to the Protease. Nexins", Cell, vol., 47, pp. 687-693, (1986).

Stone et al., "Glial-Derived Neurite-Promoting Factor is a Slow-Binding Inhibitor of Trypsin, Thrombin and Urokinase", Archives of Biochemistry and Biophysics, vol. 252, No. 1, pp. 237-244, (1987).

(Continued)

*Primary Examiner*—Robert A. Wax
*Assistant Examiner*—Suzanne M. Mayer
(74) *Attorney, Agent, or Firm*—John Prince (57) ABSTRACT

There is provided a protease inhibitor and a method of inhibiting a protease selected from the group consisting of thrombin, chymotrypsin and neuropsin, by contacting the protease with an effective amount of a member of the phosphoethanolamine binding protein (PEBP) family.

6 Claims, 2 Drawing Sheets

OTHER PUBLICATIONS

Monard et al., "Inhibition of Protease Activity Can Lead to Neurite Extension in Neuroblastoma Cells", Friedrich Miescher-Institut and Department of Biology and Center for Cancer Research, pp. 359-364.

Gurwitz et al., "Thrombin Modulates and Reverses Neuroblastoma Neurite Outgrowth", Proc. Natl. Acad. Sci. USA, vol. 85, pp. 3440-3444, (1988).

Zurn et al., "A Glia-Derived Nexin Promotes Neurite Outgrowth in Cultured Chick Sympathetic Neurons", Dev. Neurosci., vol. 10, pp. 17-24, (1988).

Farmer et al., "Glia-Derived Nexin Potentiates Neurite Extension in Hippocampal Pyramidal Cells in Vitro", Dev. Neurosci., vol., 12, pp. 73-80. (1990).

Cavanaugh et al., "Reciprocal Modulation of Astrocyte Stellation by Thrombin and Protease Nexin-1", Journal of Neurochemistry, vol., 54, No. pp. 1735-1743, (1990).

Meier et al., "Induction of Glia-Derived Nexin After Lesion of a Peripheral never", Letters to Nature, vol. 342, pp. 548-550, (1989).

Hoffmann et al., "The Prolonged Presence of Glia-Derived Nexin, an Endogenous Protease Inhibitor, in the Hippocampus after Ischemia-Induced Delayed Neuronal Death", Neuroscience, vol. 49, No. 2, pp. 397-408, (1992).

Luthi et al, "Endogenous Serine Protease Inhibitor Modulates Epileptic Activity and Hippocampal Long-Term Potentiation", The Journal of Neuroscience, vol. 17, No. 12, pp. 4688-4699, (1997).

Wolfgang J. Rettig, "Carboxypeptidase C Including Carboxypeptidase Y", Oncology Research, pp. 389-393.

Schoentgen et al., "From Structure to Function: Possible Biological Roles of a new Widespread Protein Family Binding Hydrophobic Ligands and Displaying a Nucleotide Binding Site", FEBS Letters, vol. 369, pp. 22-26, (1995).

Bernier et al., "Purification and Characterization of Basic 23 kDa Cytosolic Protein From Bovine Brain", Biochemica et Biophysica Acta., vol. 790, pp. 174-181, (1984).

Bernier et al., "Ligand Binding Studies with a 23 kDa Protein Purified from Bovine Brain Cytosol", Biochemica et Biophysica Acta, vol. 871, pp. 19-23, (1986).

Bucquoy et al., "Relationships between Molecular Interactions (Nucleotides, Lipids and Proteins) and Structural Features of the Bovine Brain 21-kDa Protein", Eur. J. Biochem, vol. 225, pp. 1203-1210, (1994).

Bollengier et al., "Isolation and Partial Biochemical characterization of an Unknown Polypeptide from White and Grey Brain Material", Neuropeptides, vol. 1, pp. 119-135, (1980).

Seddiqi et al, "Amino Acid Sequence of the Homo Sapiens Brain 21-23 kDa Protein (Neuropolypeptide h3), Comparison with its Counterparts from *Rattus Norvegicus* and *Bos Teurus* Species, and Expression of its mRNA in Different Tissues", J. Mol. Evol. vol. 39, pp. 655-660, (1994).

Schoentgen et al., "Complete Amino Acid Sequence of Basic 21-kDa Proteins from Bovine Brian Cytosol", Eur. J. Biochem, vol. 166, pp. 333-338, (1987).

Grandy et al., "Purification, Cloning, and Tissue Distribution of a 23-kDa Rat Protein Isolated by Morphine Affinity Chromatography", Molecular Endocrinology, vol. 4, No. 9, pp. 1370-1376, (1990).

Araki et al., "Isolation and Characterization of a 25-Kilodalton Protein from Mouse Testis: Sequence Homology with a Phospholipid-Biding Protein", Biology of Reproduction, vol. 47, pp. 832-843, (1992).

Perry et al., "Sequence Analysis of a Mammalian Phospholipid-Binding Protein from Testis and Epididymis and Its Distribution Between Spermatozoa and Extracellular Secretions", Biochem. J., vol. 301, pp. 235-242, (1994).

Pikielny et al., "Members of a Family of Drosphila Putative Odorant-Binding Proteins are Expressed in Different Subsets of Olfactory Hairs", Neuron, vol. 12, pp. 35-49, (1994).

Trottein et al., "The Primary Structure of a Putative Phosphatidylethanolamine-Binding Protein from *Plasmodium Falciparum*", Molecular and Biochemical Parasitology, vol. 70, pp. 235-239, (1995).

Lobos et al., "Identification of an *Onchocerca volvulus* cDNA Encoding a Low-Molecular-Weight Antigen Uniquely Recognized by Onchocerciasis Patient Sera", Molecular and Biochemical Parasitology, vol. 39, pp. 135-146, (1990).

Gems et al., "An Abundant, Trans-Spliced mRNA from Toxocara Canis Infective Larvae Encodes a 26-kDa Protein with Homology to Phosphatidylethanolamine-Binding Proteins", The Journal of Biological Chemistry, vol. 270, No. 31, pp. 18517-18522, (1995).

Robinson et al., "TFS1: A Suppressor of *cdc25* Mutations on *Saccharomyces cerevisiae*", Mol Gen Genet, vol. 230, pp. 241-250, (1991).

Ohshima et al., "Cloning and Molecular Analysis of the Arabidopsis Gene Terminal Flower 1", vol. 254, pp. 186-194, (1997).

Kardailsky et al., "Activation Tagging of the Floral Inducer *FT*", vol. 286, pp. 1962-1965, (1999).

Kobayashi et al., "A Pair of Related Genes with Antagonistic Roles in Mediating Flowering Signals", vol. 286, pp. 1960-1962, (1999).

Bradley et al., "Crontrol of Inflorescence Architecture in Antirrhinum", Nature, vol. 379, pp. 791-797, (1996).

Serre et al., "Crystal Structure of the Phosphatidylethanolamine-Binding Protein from Bovine Brain: A Novel Structural Class of Phospholipid-Binding Proteins", Structure, vol. 6, pp. 1255-1265, (1998).

Ojika et al., "Hippocampal cholinergic Neurostimulating Peptides (HCNP)", Progress in Neurobiology, vol. 60, pp. 37-83, (2000).

Bollengier et al., "Localization of the Novel Neuropolypeptide $h_3$ in Subsets of Tissues from Different Species", Journal of Neurochemistry, vol. 50, No. 4, pp. 1210-1214, (1988).

Frayne et al., "Localization of Phosphatidylethanolamine-Binding Protein in the Brain and Other Tissues", Cell Tissue Res, vol. 298, pp. 415-423, (1999).

Ott et al., "Actin-Binding Cellular Proteins Inside Human Immunodeficiency Virus Type 1", Virology, vol. 266, pp. 42-51, (2000).

Yeung et al., "suppression of Raf-1 Kinase Activity and Map Kinase Signaling by RKIP", Letters to Nature, vol. 401, pp. 173-177, (1999).

Yeung et al., "Mechanism of Suppressing of the Raf/MEK/Extracellular Signal-Regulated Kinase Pathway by the Raf Kinase Inhibitor Protein", Molecular and Cellular Biology, vol. 20, pp. 3079-3085, (2000).

Okano et al., "Myelin Basic Protein Gene and the Function of Antisense RNA in Its Repression in Myelin-Deficient Mutant Mouse", Journal of Neurochemistry, vol. 56, No. 2, pp. 560-567, (1991).

Lee et al., "Complexes Formed by (pyrimidine)$_m$-(purine)$_n$ DNA's on Lowering the PH Are All Three Stranded", Nucleic Acid Research, vol. 6, No. 9, pp. 3073-3091, (1979).

Cooney et al., "Site-Specific Oligonucleotide Binding Represses Transcription of the Human c-myc Gene in Vitro", Science, vol. 241, pp. 456-459, (1988).

Beal et al., "Second Structural Motif for Recognition of DNA by Oligonucleotide-Directed Triple-Helix Formation", Science, vol. 251, pp. 1360-1363, (1991).

Eppstein et al., "Biological Activity of Liposome-Encapsulated Murine Interferon γ is mediated by a Cell Membrane Receptor", Proc. Natl. Acad. Sci. USA, vol. 82, pp. 3688-3692, (1985).

Hwang et al., "Hepatic Uptake and Degradation of Unilamellar Sphingomyelin/Cholesterol Liposomes: A Kinetic Study", Proc. Natl. Acad. Sci. USA, vol. 77, No. 7, pp. 4030-4034, (1980).

Chomcynski et al., "Single-Step Method of RNA Isolation by Acid Guanidinium Thiocyanate-Phenol-Chloroform Extraction", Analytical Biochemistry, vol. 162, pp. 156-159, (1987).

Jalkanen et al., "Heparan Sulfate Proteoglycans from Mouse Mammary Epithelial Cells: Localization on the Cell Surface with Monoclonal Antibody", The Journal of Cell Biology, vol. 101, pp. 976-984, (1985).

Jalkanen et al., "Cell Surface Proteoglycan of Mouse Mammary Epithelial Cells is Shed by Cleavage of its Matrix-Binding Ectodomain from Its Membrane-Associated Domain", The Journal of Cell Biology, vol. 105, No. 6, pp. 3087-3096, (1987).

Stone et al., "Kinetics of the Inhibition of Thrombin by Hirudin", Biochemistry, vol. 25, pp. 4622-4628, (1986).

Dawes et al., "Monoclonal Antibodies Directed Against Human α -Thrombin and the Thrombin-Antithrombin III Complex,"Thrombosis Research, vol. 36, pp. 397-409, (1984).

Van Nostrand et al., "Purification of a Form of Protease Nexin 1 that Binds Heparin with a Low Affinity", Biochemistry, vol. 27, pp. 2176-2181, (1988).

Guenther et al., "A Glia-Derived Neurite-Promoting Factor with Protease Inhibitory Activity", The EMBO Journal, vol. 4, No. 8, pp. 1963-1966, (1985).

Shevchenko et al., "Mass Spectrometric sequencing of Protein from Silver-Stained Polyacrylamide Gels", Anal. Chem. vol. 68, pp. 850-858, (1996).

Wilm et al., "Analytical Properties of the Nanoelectrospray Ion Source", Anal. Chem. vol. 68, pp. 1-8, (1996).

Denis Monard, "Cell-Derived Proteases and Protease Inhibitors as Regulators of Neurite Outgrowth", TINS, vol. 11, No. 12, pp. 541-544, (1988).

Seeds et al., "Neuronal Migration is Retarded in Mice Lacking the Tissue Plasminogen Activator Gene", PNAS, vol. 96, No. 24, (1999).

Tsirka et al., "An Extracellular Proteolytic Cascade Promotes Neuronal Degeneration in the Mouse Hippocampus", The Journal of Neuroscience, vol., 17, No. 2, pp. 543-552. (1997).

Vaughan et al., "Thrombin Receptor Activation Protects Neurons and Astrocytes from Cell Death Produced by Environmental Insults", The Journal of Neuroscience, vol. 15, No. 7, pp. 5839-5401, (1995).

Figure 1

MAADISQWAGPLCLQEVDEPPQHALRVDYAGVTVDELGKVLTPTQVMNRP
        10        20        30        40        50

SSISWDGLDPGKLYTLVLTDPDAPSRKDPKFREWHHFLVVNMKGNDISSG
        60        70        80        90       100

TVLSDYVGSGPPSGTGLHRYVWLVYEQEQPLSCDEPILSNKSGDNRGKFK
       110       120       130       140       150

VETFRKKYNLGAPVAGTCYQAEWDDYVPKLYEQLSGK
       160       170       180

(SEQ ID NO:1)

Figure 2

SEQUENCE LISTING

```
<160> NUMBER OF SEQ ID NOS: 5

<210> SEQ ID NO 1
<211> LENGTH: 187
<212> TYPE: PRT
<213> ORGANISM: Mus musculus

<400> SEQUENCE: 1

Met Ala Ala Asp Ile Ser Gln Trp Ala Gly Pro Leu Cys Leu Gln Glu
  1               5                  10                  15

Val Asp Glu Pro Pro Gln His Ala Leu Arg Val Asp Tyr Ala Gly Val
             20                  25                  30

Thr Val Asp Glu Leu Gly Lys Val Leu Thr Pro Thr Gln Val Met Asn
         35                  40                  45

Arg Pro Ser Ser Ile Ser Trp Asp Gly Leu Asp Pro Gly Lys Leu Tyr
     50                  55                  60

Thr Leu Val Leu Thr Asp Pro Asp Ala Pro Ser Arg Lys Asp Pro Lys
 65                  70                  75                  80

Phe Arg Glu Trp His His Phe Leu Val Val Asn Met Lys Gly Asn Asp
                 85                  90                  95

Ile Ser Ser Gly Thr Val Leu Ser Asp Tyr Val Gly Ser Gly Pro Pro
            100                 105                 110

Ser Gly Thr Gly Leu His Arg Tyr Val Trp Leu Val Tyr Glu Gln Glu
        115                 120                 125

Gln Pro Leu Ser Cys Asp Glu Pro Ile Leu Ser Asn Lys Ser Gly Asp
    130                 135                 140

Asn Arg Gly Lys Phe Lys Val Glu Thr Phe Arg Lys Lys Tyr Asn Leu
145                 150                 155                 160

Gly Ala Pro Val Ala Gly Thr Cys Tyr Gln Ala Glu Trp Asp Asp Tyr
                165                 170                 175

Val Pro Lys Leu Tyr Glu Gln Leu Ser Gly Lys
            180                 185

<210> SEQ ID NO 2
<211> LENGTH: 187
<212> TYPE: PRT
<213> ORGANISM: Homo sapiens

<400> SEQUENCE: 2
```

```
Met Pro Val Asp Leu Ser Lys Trp Ser Gly Pro Leu Ser Leu Gln Glu
  1               5                  10                 15

Val Asp Glu Gln Pro Gln His Pro Leu His Val Thr Tyr Ala Gly Ala
             20                  25                 30

Ala Val Asp Glu Leu Gly Lys Val Leu Thr Pro Thr Gln Val Lys Asn
         35                  40                  45

Arg Pro Thr Ser Ile Ser Trp Asp Gly Leu Asp Ser Gly Lys Leu Tyr
     50                  55                  60

Thr Leu Val Leu Thr Asp Pro Asp Ala Pro Ser Arg Lys Asp Pro Lys
 65                  70                  75                  80

Tyr Arg Glu Trp His His Phe Leu Val Val Asn Met Lys Gly Asn Asp
                 85                  90                  95

Ile Ser Ser Gly Thr Val Leu Ser Asp Tyr Val Gly Ser Gly Pro Pro
                100                 105                 110

Lys Gly Thr Gly Leu His Arg Tyr Val Trp Leu Val Tyr Glu Gln Asp
            115                 120                 125

Arg Pro Leu Lys Cys Asp Glu Pro Ile Leu Ser Asn Arg Ser Gly Asp
        130                 135                 140

His Arg Gly Lys Phe Lys Val Ala Ser Phe Arg Lys Lys Tyr Glu Leu
145                 150                 155                 160

Arg Ala Pro Val Ala Gly Thr Cys Tyr Gln Ala Glu Trp Asp Asp Tyr
                165                 170                 175

Val Pro Lys Leu Tyr Glu Gln Leu Ser Gly Lys
                180                 185
```

<210> SEQ ID NO 3
<211> LENGTH: 27
<212> TYPE: DNA
<213> ORGANISM: artificial sequence
<220> FEATURE:
<223> OTHER INFORMATION: primer

<400> SEQUENCE: 3
ctctaagctt ccatggccgc cgacatc                                          27

<210> SEQ ID NO 4
<211> LENGTH: 66
<212> TYPE: DNA
<213> ORGANISM: artificial sequence
<220> FEATURE:
<223> OTHER INFORMATION: primer

<400> SEQUENCE: 4
tcaaagcggc cgctacttcc ctgaacagct gctcgttaca gccttgggca catagtcatc     60
ccactc                                                                 66

<210> SEQ ID NO 5
<211> LENGTH: 59
<212> TYPE: DNA
<213> ORGANISM: artificial sequence
<220> FEATURE:
<223> OTHER INFORMATION: oligonucleotide

<400> SEQUENCE: 5
tcaaagcggc cgcttaatta acgtgatggt gatggtgatg cttccctgac agctgctcg      59

METHODS AND REAGENTS FOR PROTEASE INHIBITION

TECHNICAL FIELD

The present invention relates to proteases inhibitors, useful in the fields of protein chemistry, thrombogenesis, cancer and neurobiology.

INTRODUCTION

Serine proteases are involved in many processes during tissue development and homeostasis. Among other functions they degrade components of the extracellular matrix to allow outgrowth of neuronal processes (Monard, D. (1988) *Trends Neurosci.* 11, 541–544) or cell migration (Seeds, N. W., Basham, M. E., and Haffke, S. P. (1999) *Proc. Natl. Acad. Sci. U. S. A.* 96, 4118–14123), they promote cell death (Tsirka, S. E., Rogove, A. D., Bugge, T. H., Degen, J. L., and Strickland, S. (1997) *J. Neurosci.* 17, 543–552) and act as mitogenic or survival factors (Vaughan, P. J., Pike, C. J., Cotman, C. W., and Cunningham, D. D. (1995) *J. Neurosci.* 15, 5389–5401). The activity of the proteases is regulated by their cognate inhibitors, which have to act in an accurately balanced fashion to ensure normal development and homeostasis. Disturbances of this balance in the nervous system have been proposed to be involved in pathological disorders such as Alzheimer's disease (Turgeon, V. L. and Houenou, L. J. (1997) *Brain Res. Brain Res. Rev.* 25, 85–95; Wagner S L, Geddes J W, Cotman C W, Lau A L, Gurwitz D, Isackson P J, and Cunningham D D (1989) *Proc Natl Acad Sci U S A* 86 (21):8284-8).

To date, several serine proteases have been detected in the central nervous system, including tissue type plasminogen activator (t-PA), chymotrypsin, neuropsin, elastase, and thrombin (Davies, B. J., Pickard, B. S., Steel, M., Morris, R. G., and Lathe, R. (1998) *J. Biol. Chem.* 273, 23004–23011). Many serine protease inhibitors regulating the activity of these proteases are found in the brain. However, the protease nexin-1 (PN-1; Gloor et al. (1986) Cell 47, 687–693; Stone, S. R., Nick, H., Hofsteenge, J., and Monard, D. (1987) *Arch. Biochem. Biophys.* 252, 237–244) is the only known endogenous thrombin inhibitor present in the central nervous system. In vitro, the interplay of thrombin and PN-1 has been shown to modulate neurite outgrowth of neuronal cells (Monard, D., Niday, E., Limat, A., and Solomon, F. (1983) *Prog. Brain. Res.* 58, 359–364; Gurwitz, D. and Cunningham, D. D. (1988) *Proc. Natl. Acad. Sci. U. S. A.* 85, 3440–3444; Zum et al. (1988) *Dev Neurosci* 10, 17–24; Farmer et al. (1990) *Dev. Neurosci.* 12:73–80) and the stellation of astrocytes (Cavanaugh, K. P., Gurwitz, D., Cunningham, D. D., and Bradshaw, R. A. (1990) *J. Neurochem.* 54, 1735–1743). Furthermore, PN-1 is highly expressed in response to injury of the nervous system (Meier, R., Spreyer, P., Ortmann, R., Harel, A., and Monard, D. (1989) *Nature* 342, 548–550 25; Hoffmann et al. (1992) Neuroscience 49:397–408). Despite these observations mice lacking PN-1 show only subtle phenotypes in the nervous system (Lüthi, A., Putten, H., Botteri, F. M., Mansuy, I. M., Meins, M., Frey, U., Sansig, G., Portet, C., Schmutz, M., Schroder, M., Nitsch, C., Laurent, J. P., and Monard, D. (1997) *J. Neurosci.* 17, 4688–4699), suggesting the existence of an entity that compensates for the lack of PN-1 function in these animals.

A 25 kDa carboxypeptidase Y inhibitor, termed Ic or the TFS1 gene product, has previously been described in yeast (Bruun, A. W., Svendsen, I., Sorensen, S. O., Kielland-Brandt, M. C., and Winther, J. R. (1998) *Biochemistry* 37, 3351–3357). Carboxypeptidase Y contains a catalytic Ser, His, Asp triad and a trypsin-like oxyanion hole. Its catalytic mechanism is therefore believed to be similar to the serine proteases of the trypsin-type (Mortensen, U. H., Olesen, K., and Breddam, K. (1998) in *Handbook of proteolytic enzymes* (Barrett, A. J., Rawlings, N. D., and Woessner, J. F., eds) pp. 389–393, Academic Press, London). The similarity in sequence between TFS1 (Ic) and 21–23 kDa lipid binding proteins, such as phosphatidylethanolamine binding protein (PEBP), led the authors to speculate that the 21–23 kDa lipid binding proteins may also be inhibitors of specific cellular serine carboxypeptidases. The mouse phosphatidylethanolamine-binding protein, PEBP, is made up of 187 amino acids and belongs to a family of phospholipid binding proteins found in a wide range of species from flowering plants to mammals (Schoentgen, F. and Jolles, P. (1995) *FEBS Lett.* 369, 22–26). TFS1 and mouse PEBP share 31% identity at the amino acid level.

The phosphatidylethanolamine-binding protein was originally purified from bovine brain and described as a soluble 23 kDa basic cytosolic protein (Bernier, I. and Jolles, P. (1984) *Biochim. Biophys. Acta* 790, 174–181). Binding studies revealed its affinity for phosphatidylethanolamine (Bernier, I., Tresca, J. P., and Jolles, P. (1986) *Biochim. Biophys. Acta* 871, 19–23), nucleotides like GTP and GDP and small GTP-binding proteins and other hydrophobic ligands (Bucquoy, S., Jolles, P., and Schoentgen, F. (1994) *Eur. J. Biochem.* 225, 1203–1210). Independently, PEBP was purified from human brain as neuropolypeptide h3 (Bollengier, F. and Mahler, A. (1980) *Neuropeptides* 1, 119–135 26): sequencing of this protein (Seddiqi, N., Bollengier, F., Alliel, P. M., Perin, J. P., Bonnet, F., Bucquoy, S., Jolles, P., and Schoentgen, F. (1994) *J. Mol. Evol.* 39, 655–660) showed 95% amino acid sequence identity with the sequence for the bovine PEBP (Schoentgen, F., Saccoccio, F., Jolles, J., Bernier, I., and Jolles, P. (1987) *Eur. J. Biochem.* 166, 333–338). Today members of this family have been identified in other mammals including rat (Grandy, D. K., Hanneman, E., Bunzow, J., Shih, M., Machida, C. A., Bidlack, J. M., and Civelli, O. (1990) *Mol. Endocrinol.* 4, 1370–1376), mouse (Araki, Y., Vierula, M. E., Rankin, T. L., Tulsiani, D. R., and Orgebin-Crist, M. C. (1992) *Biol. Reprod.* 47, 832–843) and monkey (Perry, A. C., Hall, L., Bell, A. E., and Jones, R. (1994) *Biochem. J.* 301 (Pt 1), 235–242). Other members of the PEBP family are the putative odorant-binding protein in *Drosphila* (Pikielny, C. W., Hasan, G., Rouyer, F., and Rosbash, M. (1994) *Neuron* 12, 35–49), the putative PEBP of the malaria parasite *Plasmodium falciparum* (Trottein, F. and Cowman, A. F. (1995) *Mol Biochem. Parasitol.* 70, 235–239), the Ov-16 antigen of *Onchocera volvulus* (Lobos, E., Altmann, M., Mengod, G., Weiss, N., Rudin, W., and Karam, M. (1990) *Mol. Biochem. Parasitol.* 39, 135–145) and the toxocara excretory-secretory antigen 26 of *Toxocara canis* (Gems, D., Ferguson, C. J., Robertson, B. D., Nieves, R., Page, A. P., Blaxter, M. L., and Maizels, R. M. (1995) *J. Biol. Chem.* 270, 18517–18522), two parasitic nematodes. A dosage-dependent suppressor of CDC25 mutations in *Saccharomyces cerevisiae*, twenty five suppressor 1 (TFS1, Robinson, L. C. and Tatchell, K. (1991) *Mol. Gen. Genet.* 230, 241–250), and several proteins in flowering plants (*Arabidopsis thaliana* (Ohshima, S., Murata, M., Sakamoto, W., Ogura, Y., and Motoyoshi, F. (1997) *Mol. Gen. Genet.* 254, 186–194 27; Kardailsky, I., Shukla, V. K., Ahn, J. H., Dagenais, N., Christensen, S. K., Nguyen, J. T., Chory, J., Harrison, M. J., and Weigel, D. (1999) *Science* 286, 1962–1965; Kobayashi, Y., Kaya, H., Goto, K., Iwabuchi, M., and Araki, T. (1999) *Science* 286, 1960–1962) and *Antirrhinum* (Bradley, D., Carpenter, R., Copsey, L., Vincent, C., Rothstein, S., and Coen, E. (1996) *Nature* 379, 791–797)) are also included in this family.

Despite this widespread expression and the resolution of the 3D structures of bovine and human PEBP by X-ray crystallography (Serre, L., Vallee, B., Bureaud, N., Schoentgen, F., and Zelwer, C. (1998) *Structure* 6, 1255–1265; Banfield, M. J., Barker, J. J., Perry, A. C., and Brady, R. L. (1998) *Structure* 6, 1245–1254) very little is known about the function or properties of the proteins in this family. In rat hippocampus, PEBP was described to be the precursor of the hippocampal neurostimulating peptide (HCNP), an undecapeptide that is involved in the differentiation of neurons in the medial septal nucleus by enhancing the synthesis of choline acetyltransferase (Ojika, K., Mitake, S., Tohdoh, N., Appel, S. H., Otsuka, Y., Katada, E., and Matsukawa, N. (2000) *Prog. Neurobiol.* 60, 37–83). However, the widespread expression of PEBP outside of the central nervous system including spleen, testis, ovary, muscle and stomach (Bollengier, F. and Mahler, A. (1988) *J. Neurochem.* 50, 1210–1214; Frayne, J., Ingram, C., Love, S., and Hall, L. (1999) *Cell. Tissue Res.* 298, 415–423) suggests additional roles for this protein.

The members of the PEBP family are often highly expressed in growing or elongated cells such as oligodendrocytes, spermatides, and the inflorescence meristem of flowering plants. Together, this expression pattern and the binding to phospholipids located mainly on the inner leaflet of the plasma membrane suggests a role for PEBP in the organization of the plasma membrane during cell growth and development. PEBP was reported to be one of several cellular proteins present inside the human immunodeficiency virus type 1 (HIV-1) virions (Ott, D. E., Coren, L. V., Johnson, D. G., Kane, B. P., Sowder, R. C., Kim, Y. D., Fisher, R. J., Zhou, X. Z., Lu, K. P., and Henderson, L. E. (2000) *Virology* 266, 42–51), supporting a possible role for PEBP in membrane organization.

On the other hand, the interaction between PEBP and small-GTP binding proteins leads to speculation that PEBP could be involved in the signaling machinery. Recently, PEBP was described as a Raf-1 kinase inhibitor protein (RKIP) that suppresses the MAP-kinase signaling (Yeung, K., Seitz, T., Li, S., Janosch, P., McFerran, B., Kaiser, C., Fee, F., Katsanakis, K. D., Rose, D. W., Mischak, H., Sedivy, J. M., and Kolch, W. (1999) *Nature* 401, 173–177; Yeung, K., Janosch, P., McFerr n, B., Rose, D. W., Mischak, H., Sedivy, J. M., and Kolch, W.(2000)*Mol. Cell. Biol.*20, 3079–3085). The authors of this study suggest that PEBP regulates the ERK pathway at the Raf/MEK interface by binding to Raf-1 and MEK thereby leading to a competitive inhibition of the ERK pathway. They further showed that the binding of PEBP/RKIP to Raf-1 decreases during mitogenic stimulation.

In summary, although possible PEBP functions have been suggested in the art, there has been no definitive demonstration of PEBP protease inhibitory activity. PEBP shares no significant homology with other known classes of serine protease inhibitors such as the serpins, the Kunitz, the Kazal, or the Bowman-Birk family (Barrett, A. J. and Salvesen, G. (1986) *Proteinase inhibitors*, Elsevier, Amsterdam 28).

SUMMARY OF THE INVENTION

According to the present invention, we provide a method of inhibiting a protease, preferably a serine protease selected from the group consisting of thrombin, chymotrypsin and neuropsin, by contacting the protease with an effective amount of a phosphoethanolamine binding protein (PEBP) family member, preferably PEBP.

The present invention also provides a screening method for identifying compounds capable of enhancing or inhibiting a biological activity of a PEBP family member, which involves contacting a protease which is inhibited by a PEBP family member with a candidate compound in the presence of a partially inhibitory amount of a PEBP family member, assaying proteolytic activity of the protease on a susceptible substrate in the presence of the candidate compound and partially inhibitory amount of the PEBP family member, and comparing the proteolytic activity to a standard level of activity, the standard being assayed when contact is made between the protease and its substrate in the presence of the partially inhibitory amount of a PEBP family member and the absence of the candidate compound. In this assay, an increase in inhibition of proteolytic activity over the standard indicates that the candidate compound is an agonist of PEBP inhibitory activity and a decrease in inhibition of proteolytic activity compared to the standard indicates that the compound is an antagonist of PEBP inhibitory activity.

In another aspect, a screening assay for agonists and antagonists is provided which involves determining the effect a candidate compound has on binding of the PEBP family member to a susceptible protease, preferably to its active site. In particular, the method involves contacting the PEBP-susceptible protease with a PEBP family member and a candidate compound and determining whether binding of the PEBP family member to the PEBP-susceptible protease is increased or decreased due to the presence of the candidate compound.

Kits comprising a phosphoethanolamine binding protein (PEBP) family member for use in any the methods of the invention are also provided.

The present invention also provides a method of inhibiting blood coagulation, comprising contacting blood with a phosphoethanolamine binding protein (PEBP) family member in an amount sufficient to inhibit blood coagulation. In this regard, receptacles and other solid surfaces that come into contact with blood can be treated with a PEBP family member, preferably PEBP, to inhibit blood coagulation. In addition, methods for treating anti-thrombogenic diseases or disorders are provided using a PEBP family member alone or in combination with other medicaments, such as an anti-coagulant.

In a further aspect of the invention, a method is provided for treating a disorder or disease, or predisposition thereto, characterized by an increase in the activity of a protease susceptible to inhibition by a PEBP family member, by administering an effective amount of a PEBP family member or an agonist thereof to an individual. Such disorders include thrombogenic disorders, neurodegenerative disorder, and cancer. Thus, also provided are compositions comprising a PEBP family member and a pharmaceutically appropriate carrier, such as liposomes for administration to an individual in need of treatment.

Methods of treatment of diseases, particularly cognitive disorders are provided and are effected by administering an effective amount of the pharmaceutical compositions. In particular, methods of treating a patient suffering from a neurodegenerative disease selected from among Alzheimer's disease, cognition deficits, Down's Syndrome, Parkinson's disease, cerebral hemorrhage with amyloidosis, dementia pugilistica, head trauma and any disorder characterized by an increase in protease activity, in particular thrombin, neuropsin or chymotrypsin activity, in the brain, by administering to the patient a therapeutically effective amount of a PEBP polypeptide.

Figure 2:
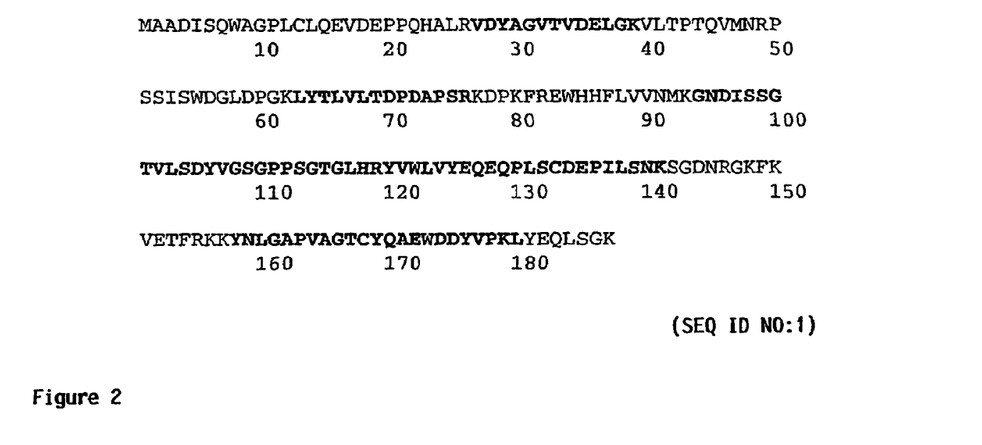

Also provided is a PEBP family member comprising the sequence provided in FIG. 2 (SEQ ID NO:1).

In a further aspect of the invention, a method is provided for diagnosing a disorder or disease characterized by an increase in the activity of a protease susceptible to inhibition by a PEBP family member, by determining whether the presence of the PEBP family member is reduced in a sample relative to a standard level, the standard level being from a non-afflicted individual.

BRIEF DESCRIPTION OF THE DRAWINGS

FIG. 1 Thrombin inhibiting activity in brains of wild type and PN-1$^{(-/-)}$ mice. Different parts of wild type (Δ, cerebellum; □, cortex; ○, remaining parts) and PN-1$^{(-/-)}$ (▲, cerebellum; ■, cortex; ●, remaining parts) brains were homogenized and their protein content measured. Aliquots with equal protein contents were stepwise diluted and assayed for thrombin inhibition.

FIG. 2 Identification of the inhibitor by NanoESI mass spectrometry. The tryptic peptides found to be identical to mouse PEBP (SEQ ID NO:1) are shown in bold. The serine at position 116 originally published (Swiss-Prot accession number P70296) was found to be a glycine that is in fact conserved in all known proteins belonging to the phosphatidylethanolamine-binding protein family. This finding was confirmed by DNA sequencing of the IMAGE clone No. 1921274 that has as the 116$_{th}$ codon a GGT instead of the previously published AGT (GenBank accession number U43206).

DETAILED DESCRIPTION OF THE INVENTION

The present inventors have identified a protease inhibitor that is able to compensate for the lack of the thrombin inhibitor, PN-1, in PN-1 (–/–) mice. The protease inhibitor has been identified as a member of the phosphatidylethanolamine binding protein (PEBP) family and has been characterized as having specific serine protease inhibitory activity, in particular thrombin, neuropsin and chymotrypsin inhibitory activities. Thus, in one aspect of the invention, a method is provided of inhibiting a protease, preferably a serine protease, more preferably a serine protease selected from the group consisting of thrombin, chymotrypsin and neuropsin, the method comprising contacting the protease with an effective amount of a phosphoethanolamine binding protein (PEBP) family member.

As used herein, the term "PEBP family member" is meant to encompass PEBP homlogues or fragments, which can be identified as such by comprising regions of at least 50% identity, preferably at least 70% identity, more preferably at least 80% identity, most preferably at least 90% identity to the regions spanning amino acid residues 65–86 and 115–128 of human PEBP as disclosed by Bruun et al. (see FIG. 1C, 3$^{rd}$ sequence therein; SEQ ID NO:2). Other than related mammalian PEBP proteins, other members of the PEBP family are the putative odorant-binding protein in *Drosphila* (Pikielny, C. W., Hasan, G., Rouyer, F., and Rosbash, M. (1994) *Neuron* 12, 35–49), the putative PEBP of the malaria parasite *Plasmodium falciparum* (Trottein, F. and Cowman, A. F. (1995) *Mol. Biochem. Parasitol.* 70, 235–239), the Ov-16 antigen of *Onchocera volvulus* (Lobos, E., Altmann, M., Mengod, G., Weiss, N., Rudin, W., and Karam, M. (1990) *Mol. Biochem. Parasitol.* 39, 135–145) and the toxocara excretory-secretory antigen 26 of *Toxocara canis* (Gems, D., Ferguson, C. J., Robertson, B. D., Nieves, R., Page, A. P., Blaxter, M. L., and Maizels, R. M. (1995) *J. Biol. Chem.* 270, 18517–18522), the TFS-1 gene product (TFS1, Robinson, L. C. and Tatchell, K. (1991) *Mol. Gen. Genet.* 230, 241–250), and several PEBPs in flowering plants (*Arabidopsis thaliana* (Ohshima, S., Murata, M., Sakamoto, W., Ogura, Y., and Motoyoshi, F. (1997) *Mol. Gen. Genet.* 254, 186–194 27; Kardailsky, I., Shukla, V. K., Ahn, J. H., Dagenais, N., Christensen, S. K., Nguyen, J. T., Chory, J., Harrison, M. J., and Weigel, D. (1999) *Science* 286, 1962–1965; Kobayashi, Y., Kaya, H., Goto, K., Iwabuchi, M., and Araki, T. (1999) *Science* 286, 1960–1962) and *Antirrhinum* (Bradley, D., Carpenter, R., Copsey, L., Vincent, C., Rothstein, S., and Coen, E. (1996) *Nature* 379, 791–797)).

Preferred members are mammalian PEBPs or synthetic PEBPs derived from the mammalian sequences, which include amino acid substitutions, deletions and additions compared to naturally occurring PEBPs. Naturally occurring PEBPs also include "allelic variants" that are alternate forms of a gene occupying a given locus on a chromosome of an organism. Genes II, Lewin, B., ed., John Wiley & Sons, New York (1985). Most preferred are human PEBP (SEQ ID NO:2) or PEBP encoded by the sequence provided in FIG. 2 (SEQ ID NO:1). Thus, in one aspect of the invention, a PEBP polypeptide encoded by the sequence provided in FIG. 2 (SEQ ID NO:1) is provided.

Although the specific examples provided herein are limited to known members of the PEBP family, it will be apparent to one of ordinary skill in the art that PEBP family members yet to be identified, or fragments thereof, are easily prepared in light of the teachings of the present specification. For example, oligonucleotide templates for the PCR-amplification of the coding sequences of the different PEBP polypeptides can be modified for use according to the extent of homology between the known and new PEBP family members and depending on hybridization conditions. Alternatively, if sufficient identity exists between the two sequences, the same template can be used without further modification. Alternatively, suitable pairs of oligonucleotide templates can be used. In addition, variants of the naturally occurring sequence is foreseen, in particular conservative substitutions of amino acids not essential for protease inhibitory activity.

The PEBP family member can be prepared as a fusion protein to facilitate purification or certain assay formats. The fusion protein may comprise, in addition to PEBP family member sequences, tags or a reporter molecule, for example. The tag can be, for example, hemagglutinin (HA), repetitive histidine residues (His6) or the like. The reporter molecule (i.e., a signal generating molecule) can be any molecule capable of providing a detectable change. Such reporter molecules include fluorescent moieties (e.g., fluorescent proteins or chemical fluorescent labels), radioactive moieties, phosphorescent moieties, antigens, reporter enzymes and the like. Preferably, the reporter molecule is a reporter enzyme whose activity brings about a detectable change. Such reporter enzymes include, but are not limited to, the following: beta-galactosidase, glucosidases, chloramphenicol acetyltransferase (CAT), glucoronidases, luciferase, peroxidases, phosphatases, oxidoreductases, dehydrogenases, transferases, isomerases, kinases, reductases, deaminases, catalases and urease. The selection of an appropriate reporter molecule will be readily apparent to those skilled in the art.

The PEBP family member or fusion protein can be easily prepared by recombinant or chemical methods, as well as by using standard protein purification techniques, as is apparent to one of ordinary skill in the art. For example, the DNA coding for the PEBP family member or fusion protein may be comprised in a nucleic acid expression cassette comprising a promoter operably linked to the nucleic acid encoding the PEBP family member or fusion protein and optionally to transcription termination signals. The fused polypeptides of the fusion protein may be connected directly or by a spacer Proteins may also be obtained by synthetic means rather than derived from natural sources, using commercially available protein synthesisers or even ordered from a commercial peptide synthesis service. Synthesized proteins may comprise any desired sequence modifications, including the use of altered amino acid residues or the addition of heterologous groups or side-chains to the polypeptide, and incorporation of labels or tags. Chemically synthesized proteins may also include non-peptidyl linkages as is apparent to those skilled in the art.

The term "effective amount" as used herein with respect to protease inhibition means sufficient to inhibit the susceptible protease by at least 20%, preferably at least 40%, more preferably at least 50% or more.

The protease inhibitory activities of PEBP family members are useful for protein purification, in particular proteinase purification (e.g., thrombin, chymotrypsin and neuropsin), as well as for other production and research applications. Thus, PEBP family members may be packaged as articles of manufacture containing packaging material, an acceptable composition comprising a PEBP polypeptide, which is effective for the desired purpose, and a label that indicates that the composition is used as a protease inhibitor, in particular an inhibitor of thrombin, chymotrypsin and neuropsin.

In one aspect of the invention, screening methods are provided where a protease susceptible to inhibition by a PEBP family member is contacted with a PEBP family member and an additional potential protease modulator. A change in the level of protease activity detected in the presence of the potential protease modulator as compared to when said potential protease modulator is absent indicates the presence of a protease modulator. The term "protease susceptible to inhibition by a PEBP family member" as used herein is meant to encompass any protease inhibited by a PEBP family member, preferably by a mammalian PEBP. Most preferably, the protease is thrombin, chymotrypsin or neuropsin.

In particular, a method is provided for identifying modulators of a biological activity of a PEBP family member, the method comprising contacting a protease susceptible to inhibition by a PEBP family member with a candidate compound in the presence of a partially inhibitory amount of said PEBP family member, assaying proteolytic activity of said protease in the presence of a susceptible substrate, said candidate compound and partially inhibitory amount of said PEBP family member, and comparing the proteolytic activity to a standard level of activity, the standard level of activity being assayed when contact is made between the protease and said substrate in the presence of the partially inhibitory amount of PEBP family member and the absence of said candidate compound. An increase in inhibition of proteolytic activity over the standard is correlated with the presence of an agonist of PEBP inhibitory activity, whereas a decrease in inhibition of proteolytic activity compared to the standard is correlated with the presence of an antagonist of PEBP inhibitory activity. Therefore, an agonist in the present context is a compound which increases the natural biological functions of a PEBP family member or which functions in a manner similar to a PEBP family member, while antagonists decrease or eliminate such functions.

The invention also provides a method of screening compounds to identify those that enhance or block the action of PEBP family members on proteases, based on their ability to interact with proteases, in particular with thrombin, chymotrypsin and neuropsin. Thus, a method is provided for identifying modulators of a biological activity of a PEBP family member by contacting a PEBP-susceptible protease, preferably thrombin, chymotrypsin or neuropsin, with a PEBP polypeptide and a candidate compound, and determining whether binding of the PEBP family member to said PEBP-susceptible protease is increased or decreased due to the presence of the candidate compound.

For example, a cellular extract or fraction may be prepared from a cell that expresses or comprises a molecule that binds a PEBP family member, such as a molecule of a signaling or regulatory pathway or phosphatidylethanolamine, or a body fluid can be used in the screening assays described herein. The preparation can be incubated with a labeled PEBP family member in the absence or the presence of a candidate molecule that may be a PEBP agonist or antagonist. The ability of the candidate molecule to bind the binding molecule is reflected in decreased binding of the labeled ligand. Molecules that bind gratuitously, i.e., without inducing the effects of PEBP on binding the PEBP-binding molecule, are most likely to be good antagonists. Molecules that bind well and elicit effects that are the same as or closely related to PEBP are agonists.

Another example of an assay for PEBP antagonists is a competitive assay that combines a PEBP family member and a potential antagonist of a PEBP-susceptible protease, particularly thrombin, chymotrypsin or neuropsin under appropriate conditions for a competitive inhibition assay. The PEBP family member can be labeled, such as by radioactivity, such that the number of PEBP family member molecules bound to protease molecules can be determined accurately to assess the effectiveness of the potential antagonist.

Potential antagonists include small organic molecules, peptides, polypeptides and antibodies that bind to a PEBP family member and thereby inhibit or eliminate its activity. Potential antagonists also may be small organic molecules, a peptide, a polypeptide such as a closely related protein or antibody that binds the same sites on a binding molecule, such as PEBP-susceptible protease molecule, without inducing PEBP-induced activities, thereby preventing the action of PEBP by excluding PEBP from binding.

Once the potential agonist/antagonist is identified, further analysis can be carried out to confirm the identification. Such tests are known in the art and include neurite outgrowth assays, phosphoinositide hydrolysis assays, $Ca^{2+}$ efflux assays, and platelet aggregation assays.

Other potential antagonists include antisense molecules. Antisense technology can be used to control gene expression through antisense DNA, or RNA or through triple-helix formation. Antisense techniques are discussed, for example, in Okano, J. Neurochem. 56: 560 (1991); "Oligodeoxynucleotides as Antisense Inhibitors of Gene Expression", CRC Press, Boca Raton, Fla. (1988). Triple helix formation is discussed in, for instance Lee et al., Nucleic Acids Research 6: 3073 (1979); Cooney et al., Science 241: 456 (1988); and Dervan et al., Science 251: 136((1991). The methods are based on binding of a polynucleotide to a complementary DNA or RNA. For example, the 5' coding portion of a polynucleotide that encodes the mature PEBP family member may be used to design an antisense RNA oligonucleotide of from about 10 to 40 base pairs in length. A DNA oligonucleotide is designed to be complementary to a region of the gene involved in transcription thereby preventing transcription and the production of PEBP. The antisense RNA oligonucleotide hybridizes to the mRNA in vivo and blocks translation of the mRNA molecule into PEBP polypeptide. The oligonucleotides described above can also be delivered to cells such that the antisense RNA or DNA may be expressed in vivo to inhibit production of PEBP.

The agonists and antagonists may be employed in a composition with a pharmaceutically acceptable carrier, e.g., as described below.

Serine proteases play a role in the pathology of a variety of disorders, including cerebral ischaemia, neurodegenerative disorders, cataract, myocardial ischaemia, muscular dystrophy and platelet aggregation. Thus, compounds that have activity as serine protease inhibitors are considered by those of skill in this art to be useful. For example, thrombin is a key protease in thrombogenesis. Intravascular clotting occurs frequently with shock, sepsis, cancer, obstetric complications, bums, and liver disease. Thus a thrombin inhibitor is particularly useful in inhibiting blood coagulation or preventing embolies.

In one aspect of the invention, therefore, a method is provided for inhibiting or delaying blood clotting comprising contacting blood with a PEBP family member or agonist, preferably a mammalian or human PEBP, in an amount sufficient to inhibit blood coagulation.

Blood generally clots in vitro in four to eight minutes when placed in a glass tube. Clotting is prevented if a chelating agent such as ethylenediaminetetraacetic acid (EDTA) or citrate is added to bind $Ca^{2+}$. The ability of a PEBP family member to delay blood clotting can be shown by addition of appropate amounts of the PEBP family member to blood to inhibit blood coagulation completely or delay blood coagulation beyond 8 minutes, as desired. The required amounts can be determined empirically.

Thrombotic disorders, including acute vascular diseases, such as myocardial infarction, stroke, peripheral arterial occlusion, deep vein thrombosis, pulmonary embolism, and other blood system thromboses, constitute major health risks. Such disorders are caused by either partial or total occlusion of a blood vessel by a blood clot, which consists of fibrin and platelet aggregates. Therapeutic intervention with agents that prevent or delay clot formation (i.e., anticoagulants) or with agents that dissolve blood clots (i.e., thrombolytics) is common practice. The unexpected antithrombin properties of PEBP family members can now be applied in treating such thrombotic disorders. The administered PEBP family member present in the blood during clot formation delays clotting time and/or may change the character of the clot that is formed to a looser, less stable clot.

The term "thrombotic disorder" as used herein encompasses conditions associated with or resulting from thrombosis or a tendency towards thrombosis. These conditions include conditions associated with arterial thrombosis, such as coronary artery thrombosis and resulting myocardial infarction, cerebral artery thrombosis or intracardiac thrombosis (due to, e.g., atrial fibrillation) and resulting stroke, and other peripheral arterial thrombosis and occlusion; conditions associated with venous thrombosis, such as deep venous thrombosis and pulmonary embolism; conditions associated with exposure of the patient's blood to a foreign or injured tissue surface, including diseased heart valves, mechanical heart valves, vascular grafts, and other extracorporeal devices such as intravascular cannulas, vascular access shunts in hemodialysis patients, hemodialysis machines and cardiopulmonary bypass machines; and conditions associated with coagulapathies, such as hypercoagulability and disseminated intravascular coagulopathy that are not the result of an endotoxin-initiated coagulation cascade.

The PEBP family member can be administered together with conventional antithrombotic agents, such as antiplatelet agents, anticoagulant agents (heparin), vitamin K antagonists (coumarin derivatives, warfarin) and thrombolytic agents, in dosages and by routes consistent with the usual clinical practice. [See, generally, Goodman & Gilman, The Pharmacological Basis of Therapeutics, 9th ed., McGraw-Hill, N.Y. (1996).]

Anti-thrombotic agents are also used routinely to prevent the occlusion of extracorporeal devices: intravascular cannulas, vascular access shunts in hemodialysis patients, hemodialysis machines, and cardiopulmonary bypass machines. Thus, in a further aspect of the invention, a PEBP family member is coated onto a solid surface, including without limitation those listed above, prior to contacting the surface with blood.

Serine proteases are known to have an effect on many other disorders and therefore, PEBP family members are useful in treating an individual in need of an increased level of PEBP activity (or of decreased proteolytic activity of a PEBP-susceptible protease, particularly thrombin, chymotrypsin and neuropsin) comprising administering to such an individual a pharmaceutical composition comprising an amount of a PEBP family member, particularly a mature form of the PEBP family member, effective to increase the PEBP activity level (and, thereby decrease the PEBP-susceptible protease activity) in such an individual. Such an individual may be suffering from a particular disorder or disease or merely at high risk of obtaining the disorder or disease.

The disorders or diseases include, but are not limited to: Alzheimer's disease, cognition deficits, Down's Syndrome, Parkinson's disease, Huntington's disease, and other chronic neurodegenerative diseases, cerebral hemorrhage with amyloidosis, dementia pugilistica, head trauma and conditions characterized by a degradation of the neuronal cytoskeleton resulting from a thrombolytic or hemorrhagic stroke, pulmonary emphysema, arthritis, multiple sclerosis, periodontal disease, cystic fibrosis, respiratory disease, thrombosis, cancer, cachexia, angina, glaucoma, inflamatory disorders, osteoporosis, cardiovascular disorders such as hypertension, atherosclerotic disorders such as cardiac infarction, and stroke, asthma, psoriasis, demyelinating diseases, AIDS immune deficiency, disorders of photoreceptor degeneration, and lens cataract formation, organ transplant rejection, restenosis, muscular dystrophy, renal failure, cerebral vasospasm, pancreatitis, disorders of mitogen induced cell growth and diabetic nephropathy.

As used herein, an effective amount of a compound for treating a disorder is an amount that is sufficient to ameliorate, or in some manner reduce a symptom or stop or reverse progression of a condition. Such amount may be administered as a single dosage or may be administered according to a regimen, whereby it is effective. "Treatment" as used herein covers any treatment of a disease in a mammal, particular a human, and includes:

(a) preventing the disease/condition or symptom from occurring in a subject which may be predisposed to the disease/condition or symptom but has not yet been diagnosed as having it;

(b) inhibiting the disease/condition or symptom, i.e., arresting its development; or
(c) relieving the disease/condition symptom, i.e., causing regression of the disease/condition.

A PEBP family member has now been shown to exhibit selective inhibition of thrombin, chymotrypsin and neuropsin. In addition, in vitro enzymatic activity has been demonstrated for recombinantly-expressed purified protein. See Examples 4 and 5. As noted above, PEBP compensates for the lack of PN-1 in PN-1 (−/−) mice. Protease nexin I (PN-1 or glia-derived nexin, GDN) has been shown to inhibit thrombin specifically and to promote, in vitro, neurite extension in neuroblastoma cell lines as well as primary hippocampal, and sympathetic neurons. The PN-1 gene is induced transcriptionally and protein levels are increased following rat sciatic nerve axotomy. Treatment of chick developing motoneurons, i.e. E6–E9 lumbrosacral motoneurons that normally undergo apoptosis, with PN-1 results in increased survival of motoneurons. Motoneuron death experimentally induced by sciatic nerve lesioning in mouse is also decreased by PN-1 addition. Alzheimer-diseased brain regions contain higher PN-1/thrombin complexes compared with free PNI than do normal brains suggesting that PN-1 may have a role in CNS pathology. Chymotrypsin has also been linked to Alzheimer's disease, and the localization of neuropsin to brain tissue also suggests a neurological function of these proteins.

Thus, due to the functional similarities and tissue localization between PEBP and PN-1, PEBP family members can be used for treating neurodegenerative disorders and peripheral neuropathies such as amyotrophic lateral sclerosis (ALS) or multiple sclerosis. Motoneuron or sensory neuron damage resulting from spinal cord injury also my be prevented by treatment with a PEBP family member. In addition, central nervous system diseases like Alzheimer's disease may be treated with a PEBP family member or, a small molecule agonist capable of crossing the blood-brain barrier, which agonist can be identified according to the methods of the present invention. For some treatments, it is advantageous to have the PEBP family member or agonist cross the blood-brain barrier. PEBP's ability to bind phosphatidylethanolamine facilitates liposome delivery across the blood-brain barrier.

Aside from the nervous system-related disorders described above, PN-1 has been shown to inhibit breakdown of extracellular matrix in a fibroblast tumor cell line. Such breakdown is thought to enable tumor cells to metastasize by weakening of extracellular matrix which normally prevents penetration of unrelated cells through a tissue. Thus, a PEBP family member may also be used to inhibit extracellular matrix destruction, in particular that associated with tumors secreting a PEBP-susceptible protease, for instance, neural tissue tumors secreting thrombin, chymotrypsin or neuropsin.

The composition comprising the PEBP family member will be formulated and dosed in a fashion consistent with good medical practice, taking into account the clinical condition of the individual patient (especially the side effects of treatment with PEBP family member alone), the site of delivery of the composition, the method of administration, the scheduling of administration, and other factors known to practitioners. The "effective amount" of PEBP family member for purposes herein is thus determined by such considerations.

As a general proposition, the total pharmaceutically effective amount of a PEBP family member administered parenterally per dose will be in the range of about 1 µg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day. If given continuously, the PEBP family member is typically administered at a dose rate of about 1 µg/kg/hour to about 50 µg/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing the PEBP family member may be administered peridurally, orally, rectally, parenterally, intravaginally, intraperitoneally, topically (as by powders, ointments, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration that include intravenous, intramuscular, intraperitoneal, intrasternal, subcutaneous and intraarticular injection and infusion.

The PEBP family member is also suitably administered by sustained-release systems. Suitable examples of sustained-release compositions include semi-permeable polymer matrices in the form of shaped articles, e.g., films, or mirocapsules. Liposomes comprising the PEBP family member are prepared by methods known in the art: DE 3,218,121; Epstein et al., Proc. Natl. Acad. Sci. (USA) 82:3688–3692 (1985); Hwang et al., Proc. Natl. Acad. Sci. (USA) 77:4030–4034 (1980); EP 52,322; EP 36,676; EP 88,046; EP 143,949; EP 142,641; Japanese Pat. Appl. 83–118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal PEBP therapy.

Generally, the formulations are prepared by contacting the PEBP family member (and, optionally, any cofactor which may enhance its activity) uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The PEBP family member is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of salts.

The invention also provides a composition comprising a PEBP family member and a pharmaceutically appropriate carrier, such as described above, as well as pharmaceutical packs or kits comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. Such kits can optionally comprise equipment useful in administering the composition such as an inhaler, syringes and the like.

In addition, the PEBP family members may be employed in conjunction with other therapeutic compounds. Agonists of PEBP may be employed in place of or in addition to a PEBP family member, for instance, for treating any of the disordersor diseases referred to above.

Similarly, antagonists of PEBP family members, such as anti-PEBP antibodies, may be used in a method for treating an individual in need of a decreased level of PEBP activity in the body (i.e., less inhibition of a protease susceptible to PEBP) comprising administering to such an individual a composition comprising a therapeutically effective amount of a PEBP antagonist. As noted above, elimination of PN-1 (described above) by homologous recombination leads to reduced long-term potentiation (LTP) of learning, whereas overexpression of PN-1 results in enhanced LTP of hippocampal neurons. Id. Similarly, antagonists PEBP activity capable of passing the blood-brain barrier can be used to enhance LTP of hippocampal neurons in nervous system conditions characterized by excessive PEBP expression.

As stated above, the present inventors have discovered that PEBP is able to compensate for PN-1 activity in brain, and further that PEBP inhibits serine proteases, such as thrombin, chymotrypsin and neuropsin. For a number of disorders, in particular of the central or peripheral nervous system and thrombogenesis, significantly higher or lower levels of PEBP protease inhibitory activity may be detected in certain tissues (e.g., central and peripheral nervous system tissue and testis) or bodily fluids (e.g., blood, serum, plasma, urine, seminal fluid, synovial fluid or cerebrospinal fluid) taken from an individual having such a disorder, relative to a "standard" PEBP protease inhibitory activity, i.e., the PEBP protease inhibitory activity level in healthy tissue from an individual not having the nervous system disorder. Thus, the invention provides a diagnostic method useful during diagnosis of nervous system disorders, which involves: (a) assaying the PEBP protease inhibitory activity level in cells or body fluid of an individual; (b) comparing the PEBP protease inhibitory activity level with a standard PEBP protease inhibitory level, whereby an increase or decrease in the assayed PEBP protease inhibitory level compared to the standard level (that from a non-afflicted individual) is indicative of a disorder in that individual.

By individual is intended mammalian individuals, preferably humans, including adults, children, babies and embryos or fetuses. By "measuring the level of PEBP" is intended qualitatively or quantitatively measuring or estimating the level of the PEBP activity, PEBP protein amount, or PEBP mRNA in a sample directly (e.g., by determining or estimating absolute protein level or mRNA level) or relatively (e.g., by comparing to the PEBP protein level or mRNA level in a second biological sample). Preferably, the PEBP level in the first biological sample is measured or estimated and compared to a standard PEBP level, the standard being taken from a second biological sample obtained from an individual not having the disorder or being determined by averaging levels from a population of individuals not having a disorder. As will be appreciated in the art, once a standard level is known, it can be used repeatedly as a standard for comparison.

By "biological sample" is intended any biological sample obtained from an individual, body fluid, cell line, tissue culture, or other source which contains PEBP protein or mRNA. As indicated, biological samples include body fluids (such as sera, plasma, seminal fluid, urine, synovial fluid and cerebrospinal fluid), nervous system tissue, and other tissue sources found to express PEBP. Methods for obtaining tissue biopsies and body fluids from mammals are well known in the art. Where the biological sample is to include mRNA, a tissue biopsy is the preferred source.

Total cellular RNA can be isolated from a biological sample using any suitable technique such as the single-step guanidinium-thiocyanate-phenol-chloroform method described in Chomczynski and Sacchi, Anal. Biochem. 162:156–159 (1987). Levels of PEBP mRNA are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

Assaying PEBP protein levels in a biological sample can occur using any art-known method. Preferred for assaying PEBP levels in a biological sample are antibody-based techniques or activity-based techniques. For example, PEBP expression in tissues can be studied with classical immunohistological methods. In these, the specific recognition is provided by the primary antibody (polyclonal or monoclonal) but the secondary detection system can utilize fluorescent, enzyme, or other conjugated secondary antibodies. As a result, an immunohistological staining of tissue section for pathological examination is obtained. Tissues can also be extracted, e.g., with urea and neutral detergent, for the liberation of PEBP protein for Western-blot or dot/slot assay, ELISA or RIA assays (Jalkanen, M., et al., J. Cell. Biol. 101:976–985 (1985); Jalkanen, M., et al., J. Cell. Biol. 105:3087–3096 (1987)). In this technique, which is based on the use of cationic solid phases, quantitation of PEBP protein can be accomplished using isolated PEBP protein as a standard. This technique can advantageously be applied to body fluids. PEBP-protein specific antibodies for use in the present invention can be prepared using routine procedures.

Preferred are assays of PEBP activity as described above and exemplified below. The examples below are provided solely for illustrative purposes and are not to be found limiting to the appended claims.

EXAMPLES

Example 1

Detection of Thrombin Inhibiting Activity in PN-1$^{(-/-)}$ Brains

Although PN-1 is thought to play an important role in the central nervous system, surprisingly, mice lacking PN-1 show only a subtle phenotype in the nervous system, indicating the potential existence of a molecule that compensates for the lack of PN-1 function in these animals. This example demonstrates that a serine protease inhibitor is present in brain homogenates of PN-1$^{(-/-)}$, which could function in the same way as PN-1.

Brain tissue was prepared from wild-type, C57bl/6 mice (BRL) of different ages or PN-1$^{(-/-)}$ mice and tested for protease inhibitory activity. Briefly, deeply anesthetized animals were pericardially perfused with PBS without $Ca^{2+}$ or $Mg^{2+}$ for 5–10 min to obtain blood-free brain tissue. The brain tissue was either homogenized as a whole or divided into tissue of the cerebellum, cortex and remaining parts of the brain before homogenizing each fraction. The tissue or fraction was homogenized for 40 sec using a Polytron (Kinematica GmbH) in 10 mM Hepes, pH 7.5, 0.2% Tween-20, 320 mM sucrose and 1 mM EDTA. The homogenates were cleared by centrifugation (12,000×g, 30 min, 4° C.) and the supernatants filtered through a Millex-HA 0.45 μm filter unit (Amicon).

The resulting supernatants were assayed for the presence of thrombin inhibitory activity. Human α-thrombin was prepared as described by Stone et al. (Stone, S. R. and Hofsteenge, J. (1986) *Biochemistry* 25, 4622–4628) and diluted in enzyme buffer (67 mM Tris, pH 8.0, 133 mM NaCl, 0.13% PEG-6000) to provide 0.005 pmol in the final assay mix. Stepwise dilutions (1:160; 1:80; 1:40; 1:20 and 1:10) of aliquots of the homogenate supernatants containing equal amounts of proteins (12+/−2 mg/ml determined by the Bradford assay) were prepared as samples for the assay. Eighty (80) μl of the samples were mixed with 10 μl thrombin (0.005 pmol) in a 96-well plate and incubated for 30 min at 37° C. After addition of 10 μl chromogenic substrate (H-D-Ile-Pro-Arg-para-nitroanilide, Chromogenix, 1.25 mg/ml in $H_2O$), any amidolytic activity was determined by measuring the rate of hydrolysis of the chromogenic substrate at 405 nm over 30 min using a THERMOmax microplate reader (Molecular Devices).

Figure 1:
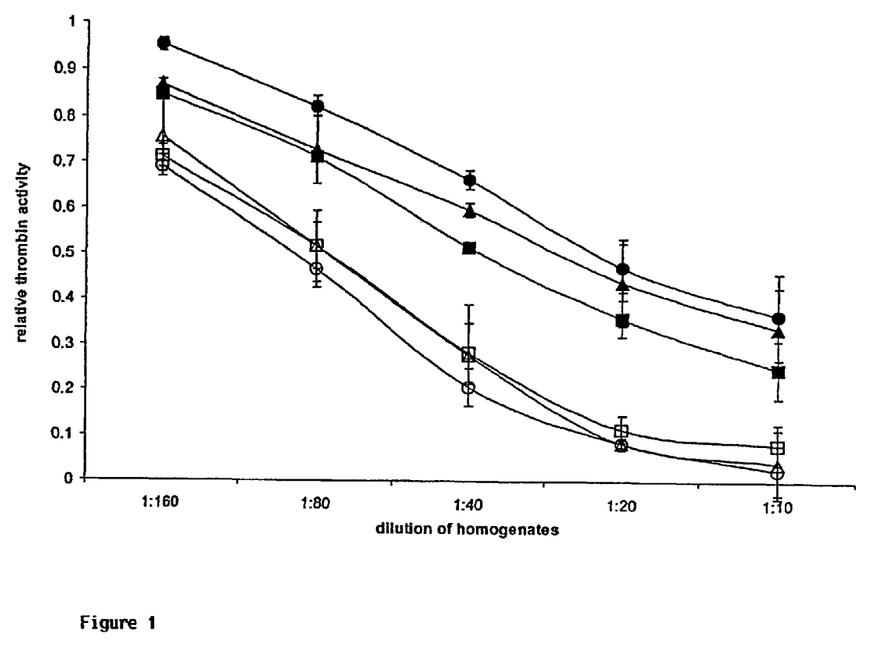

The assay revealed the presence of a thrombin inhibitory activity in all investigated brain compartments with essentially equivalent levels of activity in the various brain compartments tested here. (See FIG. 1). The presence of a thrombin inhibitor is clearly demonstrated to exist in PN-1$^{(-/-)}$ brain tissue, even though thrombin inhibition was approximately three times higher in wild type brain tissue than in PN-1$^{(-/-)}$ brain tissue. Heat treatment of PN-1$^{(-/-)}$ brain homogenates (95° C. for 5 min) completely abolishes thrombin inhibition suggesting that the inhibitory activity is due to a protein.

Example 2

Detection of Thrombin Binding Protein in PN-1$^{(-/-)}$ Brains

An electrophoretic mobility shift assay was performed to address the question as to whether a complex is formed between thrombin and one or more components of PN-1$^{(-/-)}$ brain tissue. Briefly, aliquots (8 μl and 24 μl) of whole brain homogenate supernatant (3.2 μg protein per μl), prepared as described in Example 1 from perfused PN-1$^{(-/-)}$ mice, were preincubated with 40 ng human α-thrombin in enzyme buffer in a final volume of 40 μl for 30 min at 37° C. After the preincubation step, 5 μl non-reducing sample buffer (312.5 mM Tris pH6.8, 50% glycerol and 0.05% bromophenol blue) were added and without heat denaturation of the sample prior to loading, the proteins were resolved by SDS-PAGE under non-reducing, semi-native (0.1% SDS) conditions.

The resolved proteins were electroblotted on Protran nitrocellulose transfer membrane (Schleicher-Schuell) in a trans-blot SD semi-dry transfer cell (BioRad) at 3 mA/cm$^2$ for 40 min. and analyzed for high molecular weight complexes with a polyclonal rabbit anti-human thrombin antibody (American Diagnostics, #4702) as primary antibody and an HRP-coupled donkey anti-rabbit antibody (Amersham) as secondary antibody. The western blot was visualized using the ECL detection kit (Amersham).

Preincubation of brain homogenates with thrombin in this way results in the formation of complexes of approximately 60 kDa. This size suggests a complex between thrombin (37 kDa) and a second protein of approximately 23 kDa.

To validate the formation of a complex between thrombin and a potential inhibitory protein, a co-immunoprecipitation was performed. Briefly, two whole, wild type mouse brains were homogenized as described in Example 1. One half of the sample was incubated with 60 μl human α-thrombin (1 nM) in enzyme buffer (67 mM Tris, pH 8.0, 133 mM NaCl, 0.13% PEG-6000), the other half with 60 μl enzyme buffer alone (negative control), for 30 min at 37° C. After preincubation, an immunoprecipitation was performed with protein A-Sepharose beads coated with the anti-thrombin monoclonal antibody EST-6. Protein A-Sepharose CL-4B beads (Amersham-Pharmacia) were coated with monoclonal antibodies against thrombin, EST-6 (American Diagnostics), as described elsewhere (Harlow, E. and Lane, D. (1988) in *Antibodies* (Harlow, E. and Lane, D., eds) pp. 522–523, Cold Spring Harbor Laboratory, Cold Spring Harbor, N.Y.). EST-6 is a monoclonal antibody that recognizes free thrombin as well as thrombin complexed with inhibitors (e.g. antithrombin-III) (Dawes, J., James, K., Micklem, L. R., Pepper, D. S., and Prowse, C. V. (1984) *Thromb. Res.* 36, 397–409). Fifty (50) μl of the EST-6 coated beads were added to the samples and the mixtures incubated at 4° C. overnight with gentle shaking. The beads were then washed 3 times with 1 ml enzyme buffer each, and then the co-immunoprecipitated proteins recovered by resuspending the beads in 50 μl sample buffer. After denaturation at 95° C. for 5 min, the bead supernatants were resolved by 12.5%-SDS-PAGE. The gel was then silver stained following the manufacture's protocol (BioRad Silver Stain) to visualize the proteins.

As the binding properties between thrombin and the putative inhibitor were not known initially, the co-immunoprecipitation was performed under very low stringency conditions resulting in a high background. Nevertheless a protein of approximately 20 kDa could be identified as being co-immunoprecipitated after preincubation with human α-thrombin but not with buffer.

In summary, these data suggested the existence of a thrombin binding protein of 20–23 kDa as a potential candidate thrombin inhibitor.

Example 3

Identification of Thrombin Inhibiting Activity of Thrombin Binding Protein in PN-1$^{(-/-)}$ Brains Brain homogenates were fractionated according to their molecular weights by gel filtration to establish whether the thrombin binding protein co-elutes with the moiety identified in Example 1 as having thrombin inhibitory activity. Brain homogenates (whole) from PN-1$^{(-/-)}$ of different ages (14 days; 6 months; 1 year; 2 years) or wild-type mice were prepared essentially as described in Example 1. The partial purification of the inhibitor was obtained by applying the homogenate to a Superdex 200 16/60 gel filtration column (Amersham-Pharmacia) equilibrated with 50 mM Tris, pH 8.0, 100 mM NaCl at 4° C. at a flow rate of 0.25 ml/min with the equilibration buffer. Fractions of 0.25 ml were collected and assayed for thrombin inhibiting activity.

A thrombin inhibitory activity elutes from the column in fractions no. 56–63, corresponding to an elution volume of 14–15.75 ml. Calibration of the gel filtration column with ribonuclease A (13.7 kDa), chymotrypsinogen A (25 kDa), ovalbumin (43 kDa), and bovine serum albumin (67 kDa) under the same elution conditions indicated a molecular weight for the inhibitory activity of 21–24 kDa. The amount of the 21–24 kDa inhibitory activity is approximately the same in brain homogenates prepared from mice of different ages (from 14 days to two years) as well as between wild type and PN-1$^{(-/-)}$ mice. A peak in hydrolysis rates was seen in fractions 64–66 of fractionated brain tissue from older animals, probably corresponding to a proteinase having a molecular weight of substantially less than 20 kDa, which is upregulated with age.

Further purification of the inhibitor was pursued to allow identification of the thrombin inhibitor. In previous experiments, the inhibitor was found not to bind to Q-Sepharose or heparin-Sepharose at pH 9.0 or to SP-Sepharose at pH 5.0. Because of the need to monitor activity in the flow-through or the eluate of these columns, it was not appropriate to perform the chromatography steps at higher or lower pH values. Therefore, a combined anion exchange and heparin affinity chromatography followed by a cation exchange chromatography was used to allow recovery of the inhibitor from the flow-through of the columns. The heparin column was included because of its ability to bind PN-1 whose thrombin inhibitory activity is well established (Van Nostrand, W. E., Wagner, S. L., and Cunningham, D. D. (1988) *Biochemistry* 27, 2176–2181; Guenther et al (1985) EMBO J. 4: 1963–1966).

Brain tissue homogenates for ion exchange chromatography were prepared from brain tissue of two wild type mice as in Example 1 but using 20 mM ethanolamine, pH 9.0, 100 mM NaCl, 0.2% Tween-20, 320 mM sucrose, 1 mM EDTA as homogenization buffer, and cleared of particulate material. The cleared and filtered homogenates were applied on a 1 ml HiTrap Q-Sepharose column directly connected to a 1 ml HiTrap heparin-Sepharose column (Amersham-Pharmacia) with 20 mM ethanolamine, pH 9.0, 100 mM NaCl at a flow rate of 2 ml/min. The flow-through (2 ml) was diluted with 10 ml 50 mM Acetate, pH 5.0, 70 mM NaCl and concentrated to 3 ml using a centricon YM-10 (5.000×g, 1 h, 4° C.). After exchanging the buffer with a buffer appropriate for cation exchange chromatography (50 mM Acetate, pH 5, 70 mM NaCl), the sample was loaded on a 1 ml HiTrap SP-Sepharose column (Amersham-Pharmacia) with the same buffer at a flow rate of 2 ml/min. The flow-through was concentrated to 300 µl as above. The concentrated flow-through of the HiTrap SP-Sepharose purification step was applied to a 15%-SDS-PAGE, and silver staining of the gel revealed only a single band of 20–25 kDa.

The protein separated by SDS-PAGE was excised from the gel, reduced with DTT, alkylated with iodoacetamide and cleaved with trypsin (sequencing grade, Promega) as described (Shevchenko, A., Wilm, M., Vorm, O., and Mann, M. (1996) *Anal. Chem.* 68, 850–858). The extracted tryptic peptides were desalted with 5% formic acid, 5% methanol in H$_2$O on a 1 µl Poros P20 column and concentrated to 1 µl with 5% formic acid, 50% methanol in H$_2$O directly into the nanoelectrospray ionization (NanoESI) needle. NanoESI mass spectrometry (MS) was performed according to the published method of Wilm et al. (Wilm, M. and Mann, M. (1996) *Anal. Chem.* 68, 1–8). The mass spectra were acquired on an API 300 mass spectrometer (PE Sciex) equipped with a NanoESI source (Protana).

Sequence tags from five peptides were obtained that all fitted to the amino acid sequence of the mouse phosphatidylethanolamine-binding protein (GenBank accession number P70296), with the exception that the serine at position 116 of the GenBank P70296 sequence was found to be a glycine (SEQ ID NO:1).

Example 4

Recombinant Expression of Mouse PEBP

Recombinant PEBP was prepared to establish that it is able to act as a protease inhibitor. A cDNA coding for the mouse PEBP was amplified using Pwo DNA polymerase (Roche), the IMAGE clone 1921274 (Sugano mouse, kidney) as template and appropriate primers. Sequencing of the 1921274 clone showed that the 3'-end of this cDNA is altered compared to the published sequences for the mouse PEBP-mRNA (GenBank accession number U43206) resulting in a replacement of the last ten amino acid of the PEBP. Consequently we used an antisense primer in the PCR that codes for the correct last ten amino acids. The cDNA amplified with this primer was cloned via the Not I and Hind III sites into the pCEP-Pu expression vector, i.e., pCEP4 (Invitrogen) with a puromycin instead of a hygromycin resistance gene, under the control of a CMV promoter. The correct structure of all constructs was confirmed by DNA sequencing. The sequencing reactions were performed using Dye Terminators (BigDye, PE Biosystems) with a Perkin-Elmer GeneAmp PCR system 9700 or 2400 thermocycler and analyzed on an ABI PRISM 377 DNA sequencer.

The pCEP-Pu-PEBP construct and the empty vector as a negative control were transfected into Rat-1 cells (ATCC). Alternative cells may be used, such as COS-7 cells. Rat-1 cells (1.2×10$^5$) were plated onto a 60-mm cell culture dish in 2 ml normal growth medium (Dulbecco's modified Eagle's medium with 10% fetal calf serum). After 24 h, the cells were transfected with 4 µg pCEP-Pu-PEBP or pCEP-Pu using the FuGENE 6 transfection reagent (Roche) according to supplier's instructions. The growth medium was exchanged to DMEM without serum supplemented with 5 µg/ml insulin, 5 µg/ml transferrin, 5 ng/ml sodium selenite, 16 µg/ml putrescin, and 10 ng/ml progesterone 24 h after the transfection. After another 48 h the conditioned media were collected and aliquots (5, 10, 20, 40 and 80 µl) assayed for thrombin inhibitory activity. The medium conditioned by the PEBP transfected cells showed a significant increase in inhibition of thrombin compared to the supernatant of the control cells, with inhibitory activity increasing with increasing amount of conditioned medium added.

To show that the inhibitory activity detected is indeed due to PEBP, Rat-1 were transfected with pCEP-PU-PEBP-HA. The cDNA coding for the mouse PEBP with a C-terminal hemagglutinin-tag (PEBP-HA) was amplified from the IMAGE clone 1921274 (Sugano mouse, kidney) as described above using appropriate primers introducing an HA tag. The PCR product was cloned via the Not I and Hind III sites into the expression vector pCEP-Pu under the control of a CMV promoter. The correct structure of the construct was confirmed by DNA sequencing as above. Rat-1 cells were transfected with pCEP-Pu-PEBP-HA (4 µg) and transfected cells grown essentially as described above.

The presence of HA-tagged PEBP was determined in cell lysates as well as the conditioned medium using an anti-HA antibody. In brief, conditioned medium was collected and TCA precipitated, whereas cells were lysed in SDS-sample buffer. Twenty (20) µg total protein of the cell lysates or the TCA-precipitated proteins of 1 ml conditioned medium (dissolved in sample buffer) were resolved by 12.5%-SDS-PAGE, electrotransferred to a nitrocellulose membrane and detected with an anti-[HA]-peroxidase conjugate (Roche).

PEBP-HA could be detected in the cell lysate as an approximately 25–30 kDa band on the membrane, and to a lesser extent also in the conditioned medium. Thrombin assays with the lysate and the conditioned medium of these cells carried out as described in Example 1 revealed an increase in inhibitory activity as well.

As PEBP is thought to be a cytoplasmic protein and lacks a secretion signal in its sequence, it was somehow unexpected to detect it in the conditioned medium of PEBP-expressing cells. To validate this extracellular localization of PEBP, RAT-1 cells were transfected with pCEP-Pu-HA-PEBP-IRES-GFP, a construct encoding HA tagged PEBP fused to green fluorescent protein (GFP). The cDNA coding for the mouse PEBP with a N-terminal hemagglutinin-tag (HA-PEBP) was amplified essentially as described above using appropriate primers to introduce an N-terminal HA tag. The PCR product was cloned via the Not I and Hind III sites into the expression vector pCEP-Pu-IRES-GFP under the control of a CMV promoter. The correct structure of the construct was confirmed by DNA sequencing as above.

Rat-1 cells were transfected with pCEP-Pu-HA-PEBP-IRES-GFP essentially as described above. 48 h after transfection the growth medium was aspirated, the cells were washed 3 times with phosphate buffered saline (PBS), fixed for 20 min. with 4% paraformaldehyde in PBS, and again washed with PBS. After blocking for 30 min. with 3% BSA in PBS the cells were incubated with a rhodamine-anti-[HA]-conjugate (Roche) in blocking solution for 1 hr and washed with PBS. For permeabilization, the cells were fixed in 4% paraformaldehyde with 15% picric acid, PBS with 0.2% Triton-X 100 was used, and the cells were incubated prior to blocking in 1.5 M Tris, pH 8.8, 0.4% SDS.

The Rat-1 cells transfected with an HA-PEBP-IRES-GFP construct displayed HA-PEBP on their surface. Non permeabilized and permeabilized cells were immunostained with an anti-[HA]-rhodamine conjugate, and both non-permeabilized and permeabilized cells were shown to be stained at the cell surface and cytoplasm.

The amino acid sequence of PEBP contains no obvious secretion signal and previous immunohistochemical studies attributed a cytoplasmic localization to this protein. The existence of active PEBP in the supernatant of transfected cells and the immunodetection of HA-tagged PEBP on the cell surface shown here, demonstrate that at least in vitro the localization of PEBP is not restricted to the cytoplasm or the inner leaflet of the plasma membrane. As HA-positive but non-transfected (GFP-negative) cells were not observed, the HA-immunoreactivity is not due to binding of HA-PEBP released to the medium by possibly dying cells.

Example 5

Protease Inhibition Profile of PEBP

To evaluate the inhibitory profile of PEBP, RAT-1 cells were transfected with a construct coding for PEBP with a 6×His-tag at the N-terminus. The cDNA coding for the mouse PEBP was amplified with Pwo DNA polymerase (Roche) from the IMAGE clone 1921274 (Sugano mouse, kidney) using appropriate primers (5'-CTC TAA GCT TCC ATG GCC GCC GAC ATC-3', SEQ ID NO:3; and 5'-TCA AAG CGG CCG CTA CTT CCC TGA ACA GCT GCT CGT TAC AGC CTT GGG CAC ATA GTC ATC CCA CTC-3', SEQ ID NO:4). The PCR product was cloned via the Not I and Hind III sites into the expression vectors pCEP-Pu under the control of a CMV promoter. A cDNA coding for PEBP with a stretch of six histidine residues fused to the carboxy-terminus was amplified from this construct using the oligonucleotides 5' CTC TAA GCT TCC ATG GCC GCC GAC ATC-3', SEQ ID NO:3; and 5'-TCA AAG CGG CCG CTT AAT TAA CGT GAT GGT GAT GGT GAT GCT TCC CTG ACA GCT GCT CG-3'; SEQ ID NO:5. The correct structure of all constructs was confirmed by DNA sequencing as above.

Rat-1 cells ($4\times10^5$) were plated in 10-cm cell culture dishes and after 24 h transfected with 16 μg pCEP-Pu-6×His-PEBP or pCEP-Pu essentially as described above in Example 4. After a further 24 h, the medium was exchanged to serum-free DMEM with supplement. 72 h after transfection the medium was collected from four dishes and the cells lysed in 600 μl enzyme buffer (67 mM Tris, pH 8.0, 133 mM NaCl, 0.13% PEG-6000) containing 10 mM imidazole. The recombinant 6×His-PEBP protein was purified using the Ni-NTA Spin Kit (Qiagen) under native conditions following the manufacture's protocol with enzyme buffer containing 20 mM imidazole as washing buffer and enzyme buffer containing 250 mM imidazole as elution buffer. The eluate was desalted over a NAP-5 column to remove the imidazole resulting in a total volume of 1 ml. Cell lysate of "empty" vector transfected cells was treated in the same way and served as control. Alternatively, 20 mM sodium phosphate pH6.8, 320 mM sucrose, 0.2% TWEEN-20 and 1 mM EDTA can be used as enzyme buffer.

Six different serine proteases were diluted in enzyme buffer (67 mM Tris, pH 8.0, 133 mM NaCl, 0.13% PEG-6000) and used in protease activity assays with the following final amounts: thrombin, trypsin and chymotrypsin, 0.005 pmol; t-PA and neuropsin, 0.5 pmol; and pancreatic elastase, 4 pmol. Human α-thrombin was prepared and according to Stone et al. (Stone, S. R. and Hofsteenge, J. (1986) *Biochemistry* 25, 4622–4628); all other proteases are commercially available (e.g., Sigma, Fluka). Each diluted protease (10 μl) was preincubated with 80 μl of a 6×His-PEBP preparation that had been shown to inhibit the amidolytic activity of 0.005 pmol thrombin to approx. 55%. The pre-incubation was carried out in a 96-well plate for 30 min at 37° C. After addition of 10 μl chromogenic protease substrate (H-D-Ile-Pro-Arg-para-nitroanilide, Chromogenix, 1.25 mg/ml in $H_2O$ for all proteases other than chymotrypsin; or N-Succinyl-Ala-Ala-Pro-Phe-para-nitroanilide, Sigma, 2.3 mg/ml in $H_2O$ for chymotrypsin), any remaining amidolytic activity was determined by measuring the rate of hydrolysis of the chromogenic substrate at 405 nm over 30 min using a THERMOmax microplate reader (Molecular Devices). The 6×His-PEBP sample caused a 25% inhibition of 0.005 pmol chymotrypsin and a 70% inhibition of 0.5 pmol neuropsin. The amidolytic activities of trypsin (0.005 pmol), tissue plasminogen activator (0.5 pmol), and pancreatic elastase (4 pmol) were not affected.

To determine the inhibition constants, the rates for the hydrolysis of the chromogenic substrates were measured as described above at fixed enzyme concentrations and substrate concentrations ranging from 3.5 μM to 216 μM and PEBP-H6 concentrations between 0 and 2.9 μM. The measured values were fitted with the software GraFit 4.0 (Erithacus Software) to the equation for a competitive inhibitor. Thrombin and chymotrypsin are competitively inhibited by PEBP-H6 with apparent $K_i$ of $3.8+/-1.3\times10^{-7}$ and $1.8+/-1.0\times10^{-6}$, respectively.

An interference of the C-terminal histidine tag could be excluded by the use of purified N-terminal His-tagged PEBP, partially purified PEBP with an N- or C-terminal hemagglutinin tag, as well as the protein encoded by the IMAGE clone No. 1921274 with 10 different amino acids at the C-terminal. All these different proteins showed similar inhibitory properties.

In summary, a serine protease inhibitor from brain tissue, PEBP, is demonstrated to inhibit the amidolytic activities of thrombin, neuropsin, and chymotrypsin, but not trypsin, tissue-type plasminogen activator (t-PA), or pancreatic elastase. Data supporting PEBP's inability to inhibit the serine proteases kallikrein and activated protein C were also obtained using partially purified PEBP fractions.

Example 6

Preparation of Antibodies Against PEBP and Localization of PEBP

In order to raise a polyclonal antiserum against PEBP, two C-terminal peptides of the mouse PEBP (amino acids 144–159 and 174–187) were crosslinked to ovalbumin and injected into rabbits following standard protocols. The specificity of the immune serum was assessed by the detection of a single 21 kDa band on immunoblots of mouse brain homogenate.

Rat-1 fibroblasts were washed 3 times with PBS, fixed for 20 min with 4% paraformaldehyde in PBS at room temperature, and again washed with PBS. For permeabilization, the cells were fixed in 4% paraformaldehyde with 15% picric acid in PBS (20 min, room temperature) and washed with PBS with 0.2% Triton-X 100. After blocking for 30 min with 3% BSA in PBS the cells were incubated for one hour with antiserum (1:1500 in blocking solution) and then washed with PBS. Immunofluorescence detection was performed using the Alexa 488 goat anti-rabbit IgG conjugate (Molecular Probes) as secondary antibody. PEBP-immunoreactivity was seen in permeabilized and non-permeabilized cells. The detection of PEBP-immunoreactivity at the surface of non-permeabilized Rat-1 cells supports an extracellular localization of PEBP, in addition to its cytoplasmic localization.

All publications cited in this specification are herein incorporated by reference as if each individual publication were specifically and individually indicated to be incorporated by reference herein as though fully set forth.

What is claimed is:

1. A method of inhibiting the protease thrombin, said method comprising contacting said protease with an effective amount of a phosphoethanolamine binding protein (PEBP) family member.

2. The method of claim 1, wherein said protease is thrombin.

3. The method of claim 1, wherein said PEBP family member is a mammalian PEBP or a fragment thereof.

4. The method of claim 3, wherein said PEBP family member is human PEBP.

5. The method of claim 3, wherein said PEBP is encoded by the sequence provided in FIG. 2.

6. The method of claim 1, further comprising contacting said protease and protease inhibitor with a potential protease modulator and determining a change in the level of protease activity as compared to when said protease inhibitor is absent.

* * * * *